(12) United States Patent
Bradley et al.

(10) Patent No.: US 8,688,233 B2
(45) Date of Patent: Apr. 1, 2014

(54) SYSTEM AND METHOD FOR SPINAL CORD STIMULATION TO TREAT MOTOR DISORDERS

(75) Inventors: Kerry Bradley, Grendale, CA (US); Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/529,906

(22) Filed: Jun. 21, 2012

(65) Prior Publication Data
US 2012/0330391 A1 Dec. 27, 2012

Related U.S. Application Data

(60) Provisional application No. 61/500,557, filed on Jun. 23, 2011.

(51) Int. Cl.
*A61N 1/05* (2006.01)

(52) U.S. Cl.
USPC .......................................................... 607/117

(58) Field of Classification Search
USPC .......................................................... 607/117
See application file for complete search history.

(56) References Cited

U.S. PATENT DOCUMENTS

| | | | |
|---|---|---|---|
| 5,501,703 A * | 3/1996 | Holsheimer et al. | 607/46 |
| 6,895,280 B2 | 5/2005 | Meadows et al. | |
| 7,529,582 B1 * | 5/2009 | DiLorenzo | 607/2 |
| 7,650,184 B2 | 1/2010 | Walter | |
| 7,987,000 B2 | 7/2011 | Moffitt et al. | |
| 8,019,439 B2 | 9/2011 | Kuzma et al. | |
| 2007/0150036 A1 | 6/2007 | Anderson | |
| 2007/0168007 A1 | 7/2007 | Kuzma et al. | |
| 2010/0057162 A1 | 3/2010 | Moffitt et al. | |
| 2012/0165898 A1 | 6/2012 | Moffitt | |
| 2012/0215218 A1 * | 8/2012 | Lipani | 606/41 |

OTHER PUBLICATIONS

U.S. Appl. No. 61/427,441, Neurostimulation System for Selectively Estimating Volume of Activation and Providing Therapy, Inventor: Michael A. Moffit et al., filed Dec. 27, 2010.

* cited by examiner

*Primary Examiner* — George Manuel
(74) *Attorney, Agent, or Firm* — Vista IP Law Group LLP

(57) ABSTRACT

A method for using spinal cord stimulation to treat symptoms of motor disorders includes implanting a stimulation lead within a ventral portion of the epidural space. The lead is implanted with at least a portion of the electrodes facing the spinal cord. In a method for providing therapy to a patient suffering from a motor disorder, electrical stimulation energy is applied to at least one ventral column nerve fiber through the implanted stimulation lead. A peripheral region of the patient's body exhibits the symptoms of the motor disorder, and the ventral column nerve fiber to which the stimulation is applied innervates that peripheral region.

11 Claims, 11 Drawing Sheets

SYSTEM AND METHOD FOR SPINAL CORD STIMULATION TO TREAT MOTOR DISORDERS

RELATED APPLICATION DATA

The present application claims the benefit under 35 U.S.C. §119 to U.S. provisional patent application Ser. No. 61/500,557, filed Jun. 23, 2011. The foregoing application is hereby incorporated by reference into the present application in its entirety.

FIELD OF THE INVENTION

The present inventions relate to systems and methods for treating motor disorders using spinal cord stimulation.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic pain syndromes, and the application of spinal cord stimulation has expanded to additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue (e.g., the dorsal column) of the patient, and a neurostimulator implanted remotely from the stimulation site, but coupled either directly to the stimulation lead(s) or indirectly to the stimulation lead(s) via a lead extension. The neurostimulation system may further comprise a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which when strong enough, depolarizes (or "stimulates") the neural fibers within the spinal cord beyond a threshold level, thereby inducing the firing of action potentials (APs) that propagate along the neural fibers to provide the desired efficacious therapy to the patient.

As briefly discussed above, SCS may be to treat patients suffering from motor disorders. Symptoms of motor disorders may be the result of control issues driven by sensory input. A patient with a motor disorder may have a healthy motor cortex, but the input to the motor cortex may be inappropriate. An imbalance between excitatory and inhibitory input into the motor cortex may result in motor disorder symptoms, such as tremor, bradykinesia, abnormal gait, akinesia, and the like. Sensory input travels to the motor cortex via sensory nerves in the dorsal column. Thus, in an effort to restore balance between the excitatory and inhibitory inputs into the motor cortex, stimulation is applied to the dorsal column of the spinal cord in conventional SCS treatments for motor disorders. In order to apply stimulation to the dorsal column 102, the stimulation lead 12 is positioned in the dorsal region 122 of the epidural space 120, as shown in cross-section in FIG. 1. Such dorsal column stimulation for treating symptoms of motor disorders has not yet found widespread use, however, because long-term efficacy in a large number of patients has not been demonstrated. Anecdotal successes have been observed with dorsal column stimulation for motor disorders, but there have been patients who have received no demonstrable benefit. Since SCS is a minimally-invasive approach, SCS techniques for effectively managing symptoms of motor disorders remain attractive in comparison to brain-stimulation-based methods such as Motor Cortex Stimulation or Deep Brain Stimulation.

SUMMARY OF THE INVENTION

In accordance with a first aspect of the present inventions, a method for of performing a medical procedure on a patient suffering from a motor disorder is provided. The method uses a stimulation lead having at least one electrode. The lead may be a paddle lead and the at least one electrode may be a plurality of electrodes disposed on the same side of the paddle lead. Alternatively, the lead may be a cylindrical lead and the at least one electrode may be a plurality of radially segmented electrodes or a plurality of ring electrodes.

The method in accordance with the first aspect includes introducing a stimulation lead having at least one electrode within a ventral portion of an epidural space of the patient, facing at least a portion of the at least one electrode toward a spinal cord of the patient, and affixing the lead within the patient, such that the portion of the at least one electrode faces the spinal cord. The lead may be affixed parallel to the spinal cord. The motor disorder may affect a peripheral region of the patient, and the lead may be affixed such that the at least one electrode is located at an area of the spinal cord having at least one ventral column nerve fiber that innervates the peripheral region.

In accordance with a second aspect of the present inventions, a method for providing therapy to a patient suffering from a motor disorder is provided. The method uses at least one electrode implanted within a ventral portion of an epidural space of the patient. The method includes applying electrical stimulation energy to at least one ventral column nerve fiber of the patient, thereby treating symptoms of the motor disorder. The applied electrical stimulation energy may inhibit nerve impulses traveling from the patient's brain to a peripheral region exhibiting the symptoms of the motor disorder. The motor disorder may affect a peripheral region of the patient, and the at least one ventral column nerve fiber may innervate the peripheral region. The electrical stimulation energy may be applied at a frequency above 100 Hz and a pulse width of less than 20 µs.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 2:
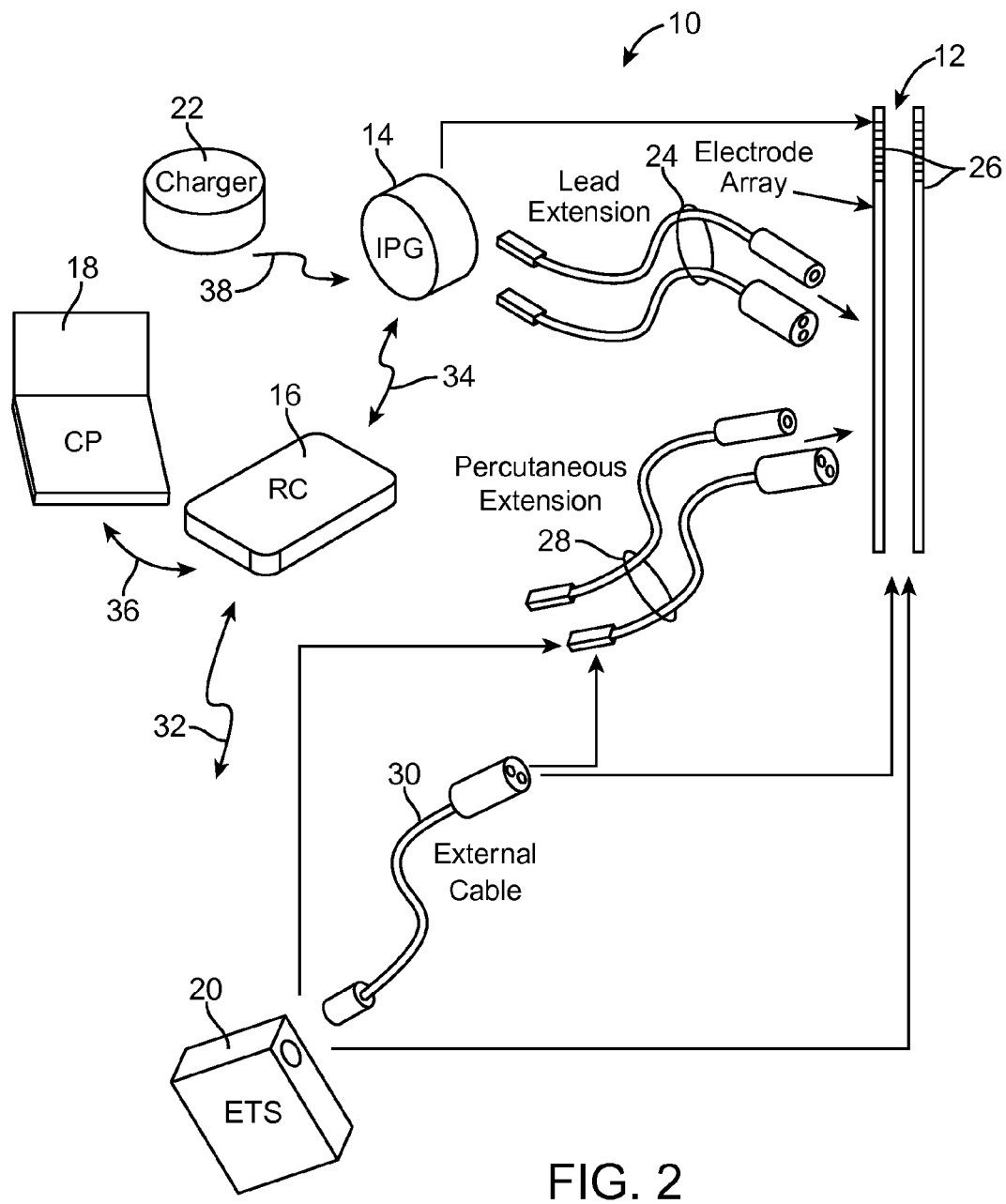
FIG. 2 is a plan view of an embodiment of a spinal cord stimulation (SCS) system arranged in accordance with the present inventions.

Turning first to FIG. 2, an exemplary SCS system 10 generally includes one or more (in this case, two) implantable stimulation leads 12, an implantable pulse source (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has pulse generation circuitry similar to that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used, on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 3:
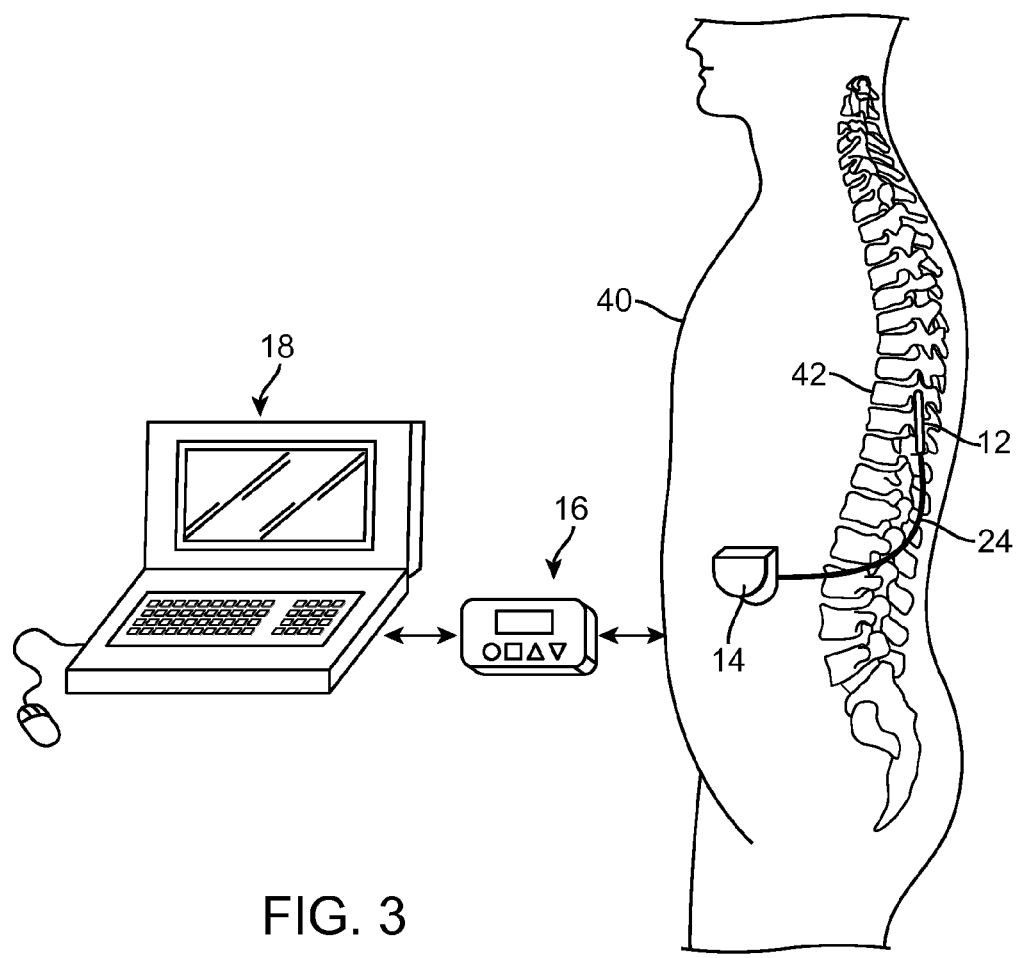
FIG. 3 is a plan view of the SCS system of FIG. 2 in use within a patient.

As shown in FIG. 3, the stimulation leads 12 are implanted within the spinal column 42 of a patient 40. In general, the leads 12 are implanted parallel to the spinal cord and at the midline of the patient's body. Due to the lack of space near the location where the stimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the stimulation leads 12. As there shown, the CP 18 communicates with the IPG 14 via the RC 16.

Referring now to FIGS. 4A-4D, the external features of the stimulation leads 12 and the IPG 14 will be briefly described. The leads 12 and the electrodes 26 may have one of the configurations shown in FIGS. 4A-4D, which are explained in more detail below. In each of the embodiments shown in FIGS. 4A-4D, the electrodes 26 on the leads 12 may be very narrowly spaced in order to allow for very focal stimulation fields. The leads 12 may be MRI-conditionally compatible and/or MRI-safe. The actual number and shape of leads and electrodes will, of course, vary according to the intended application.

Figure 4A:
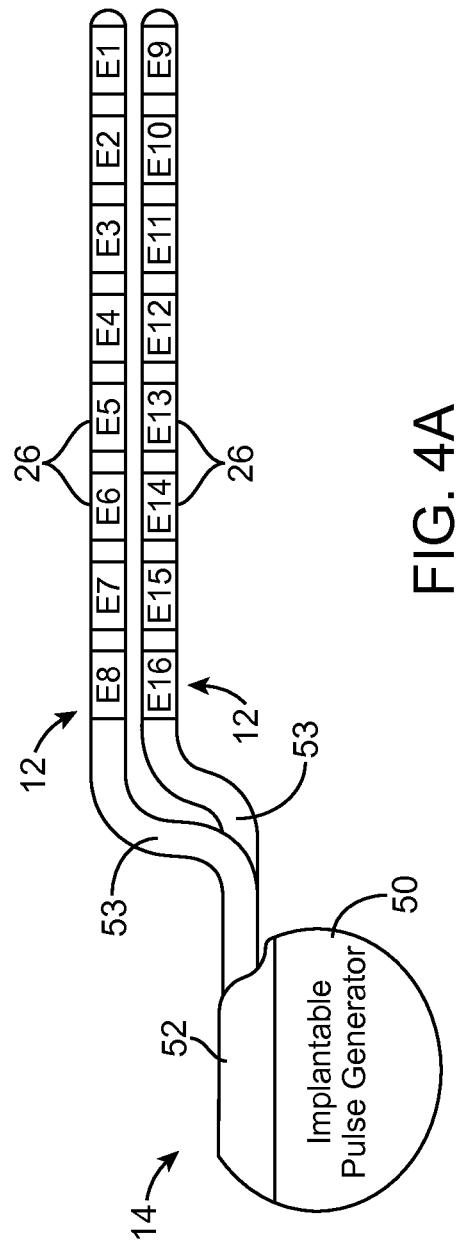
FIG. 4A is a side view of an implantable pulse generator and a pair of stimulation leads that can be used in the SCS system of FIG. 2.

In accordance with the embodiment shown in FIG. 4A, each of the stimulation leads 12 comprises an elongated cylindrical lead body 53, and the electrodes 26 take the form of ring electrodes mounted around the lead body 53. One of the stimulation leads 12 has eight electrodes 26 (labeled E1-E8), and the other stimulation lead 12 has eight electrodes 26

(labeled E9-E16). Further details describing the construction and method of manufacturing percutaneous stimulation leads having ring electrodes are disclosed in U.S. Pat. No. 7,650,184, entitled "Cylindrical Multi-Contact Electrode Lead for Neural Stimulation and Method of Making Same," and U.S. patent application Ser. No. 11/689,918, entitled "Lead Assembly and Method of Making Same," the disclosures of which are expressly incorporated herein by reference.

Figure 4B:
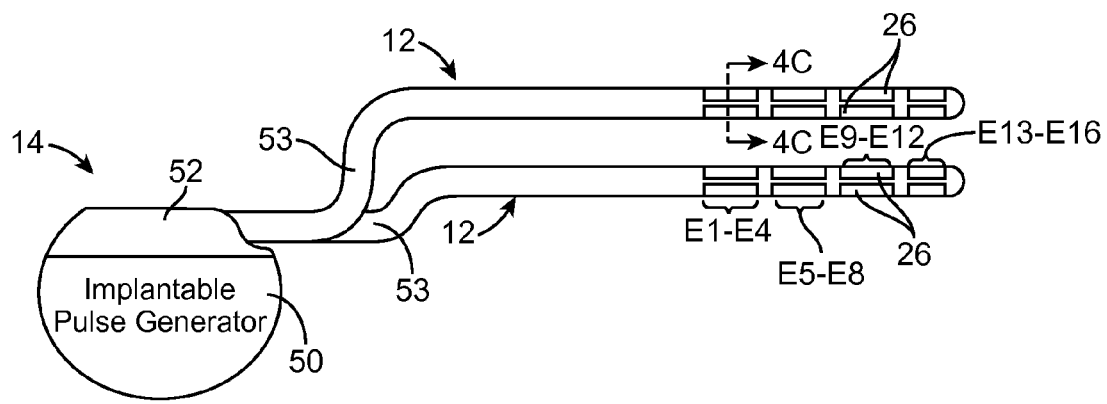
FIG. 4B is a side view of an implantable pulse generator and a second embodiment of a pair of stimulation leads that can be used in the SCS system of FIG. 2.
Figure 4C:
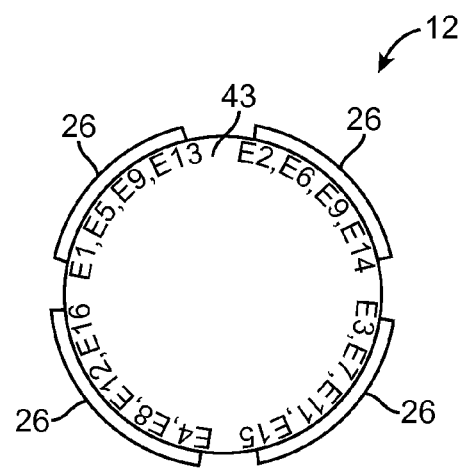
FIG. 4C is a cross-sectional view of one of the stimulation leads of FIG. 4B, taken along the line 4C-4C.

In another embodiment illustrated in FIGS. 4B and 4C, the electrodes 26 take the form of segmented electrodes that are circumferentially and axially disposed about the cylindrical lead body 53. By way of non-limiting example, one stimulation lead 12 may carry sixteen electrodes 26, arranged as four rings of electrodes (the first ring consisting of electrodes E1-E4; the second ring consisting of electrodes E5-E8; the third ring consisting of electrodes E9-E12; and the fourth ring consisting of E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). Alternatively, each ring of electrodes may include two, three, or more than four electrode segments. Further details regarding segmented circumferential electrodes may be found, for example, in Provisional U.S. Patent Application Ser. No. 61/427,441, expressly incorporated herein by reference.

Figure 4D:
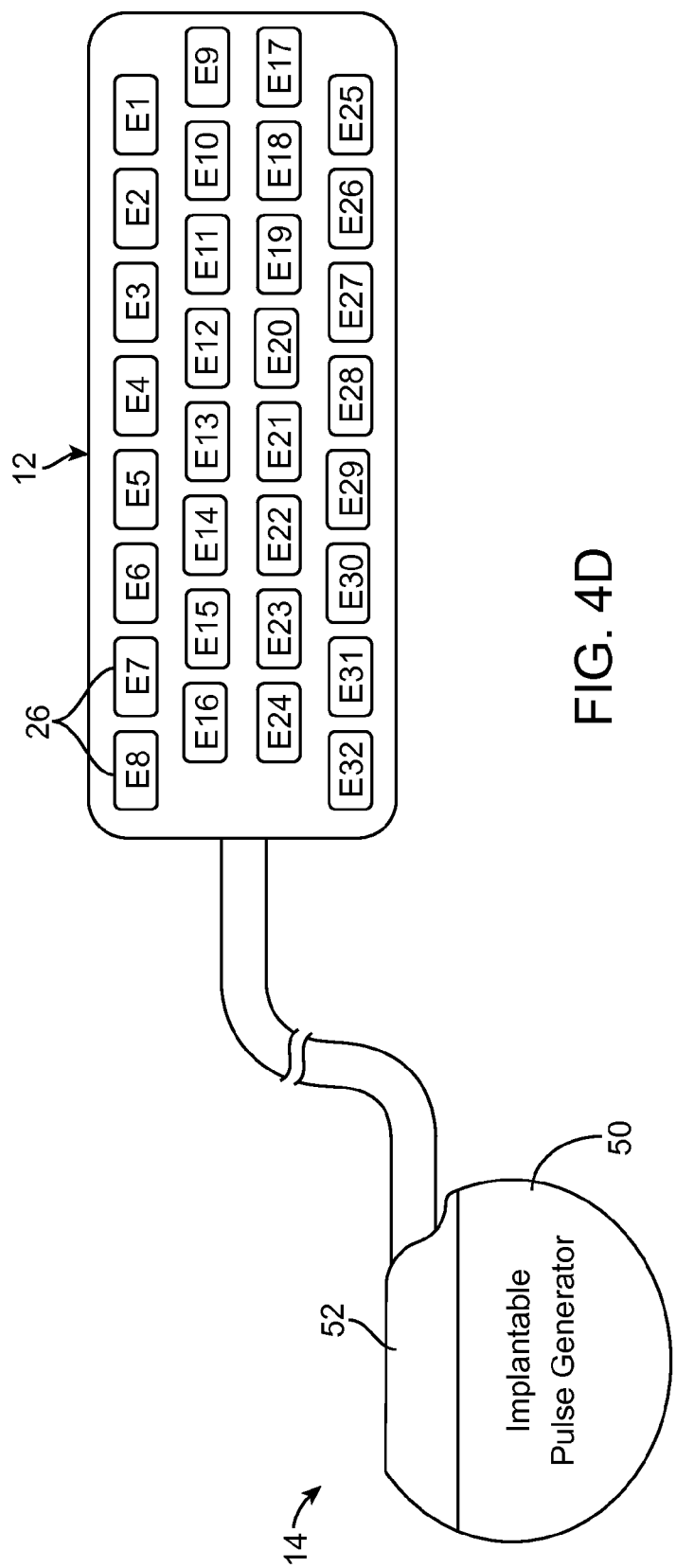
FIG. 4D is a side view of an implantable pulse generator and a surgical paddle stimulation lead that can be used in the SCS system of FIG. 2.

In yet another embodiment illustrated in FIG. 4D, the stimulation lead 12 takes the form of a surgical paddle lead 12 on which the electrodes 26 (in this case, electrodes E1-E32) are carried. The electrodes 26 are arranged in a two-dimensional array in four columns along the axis of the stimulation lead 12. Further details regarding the construction and method of manufacture of surgical paddle leads are disclosed in U.S. patent application Ser. No. 11/319,291, entitled "Stimulator Leads and Methods for Lead Fabrication," and U.S. patent application Ser. No. 12/204,094, entitled "Multiple Tunable Central Cathodes on a Paddle for Increased Medial-Lateral and Rostro-Caudal Flexibility via Current Steering," the disclosures of which are expressly incorporated herein by reference.

In each of the embodiments depicted in FIGS. 4A-4D, the IPG 14 comprises an outer case 50 for housing the electronic and other components, and a connector 52 to which the proximal ends of the stimulation leads 12 mate in a manner that electrically couples the electrodes 26 to the electronics within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 50. Simulation energy may be transmitted to the tissue in a monopolar or multipolar (e.g., bipolar, tripolar, etc.) fashion. Monopolar stimulation occurs when a selected one of the lead electrodes 26 is activated along with the case 50 of the IPG 14, so that stimulation energy is transmitted between the selected electrode 26 and the case 50. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
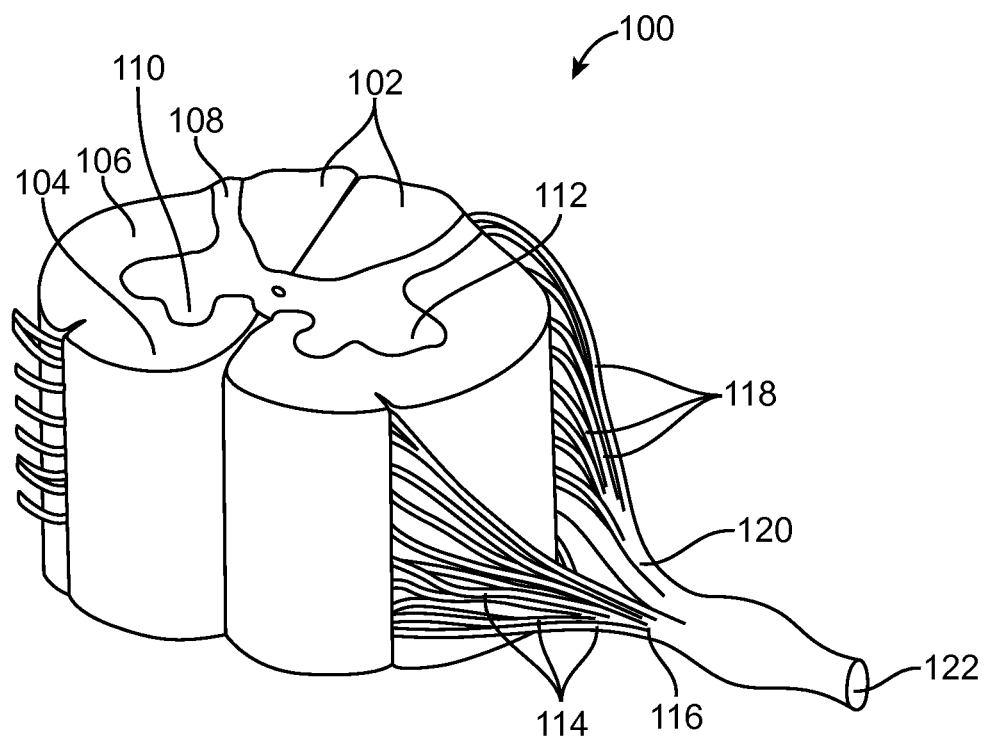
FIG. 5 is a peripheral view of the spinal cord and spinal nerves.

Referring now to FIG. 5, the portions of the spinal cord 100 that are relevant to the present inventions will be described. The spinal cord 100 is divided into three columns: the dorsal column 102, the ventral column 104, and the lateral column 106. Similarly, the butterfly-shaped gray matter of the spinal cord 100 is divided into the dorsal horn 108, the ventral horn 110, and the lateral horn 112. Motor nerve rootlets 114 branch off of the ventral horn 110 and combine to form the ventral root 116. Similarly, sensory nerve rootlets 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body.

Figure 1:
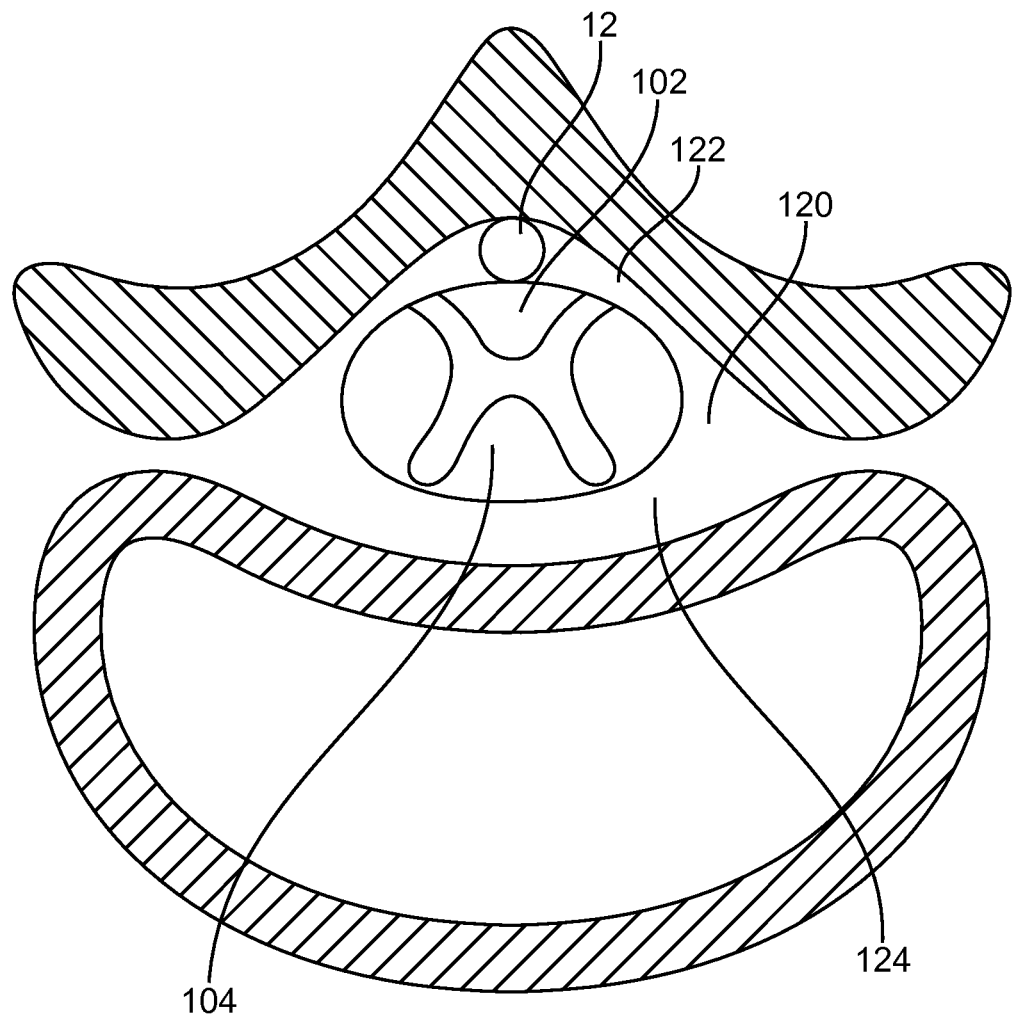
FIG. 1 is a cross-sectional view of the spinal cord showing the placement of a spinal cord stimulation lead in accordance with the prior art.
Figure 6A:
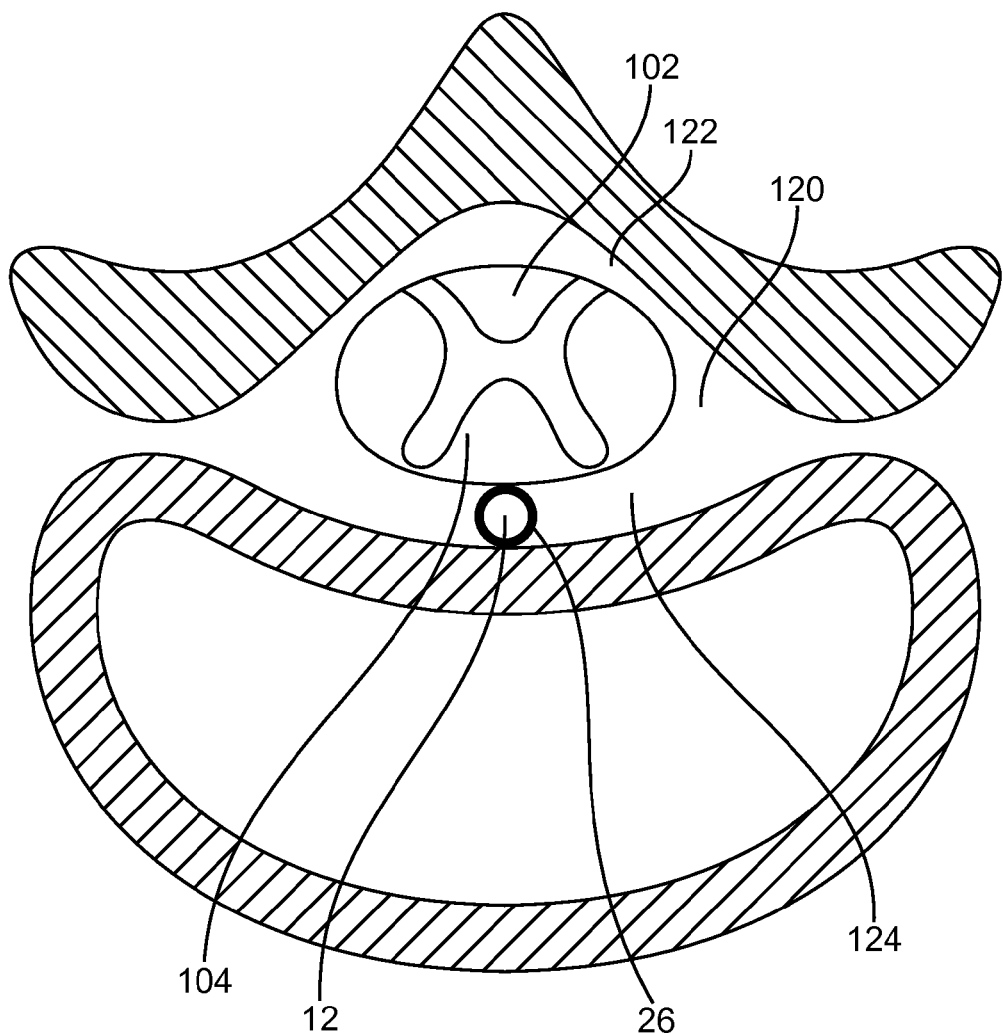
FIG. 6A is a cross-sectional view of the spinal cord showing the placement of a ring electrode on a cylindrical stimulation lead in accordance with the present inventions.
Figure 6B:
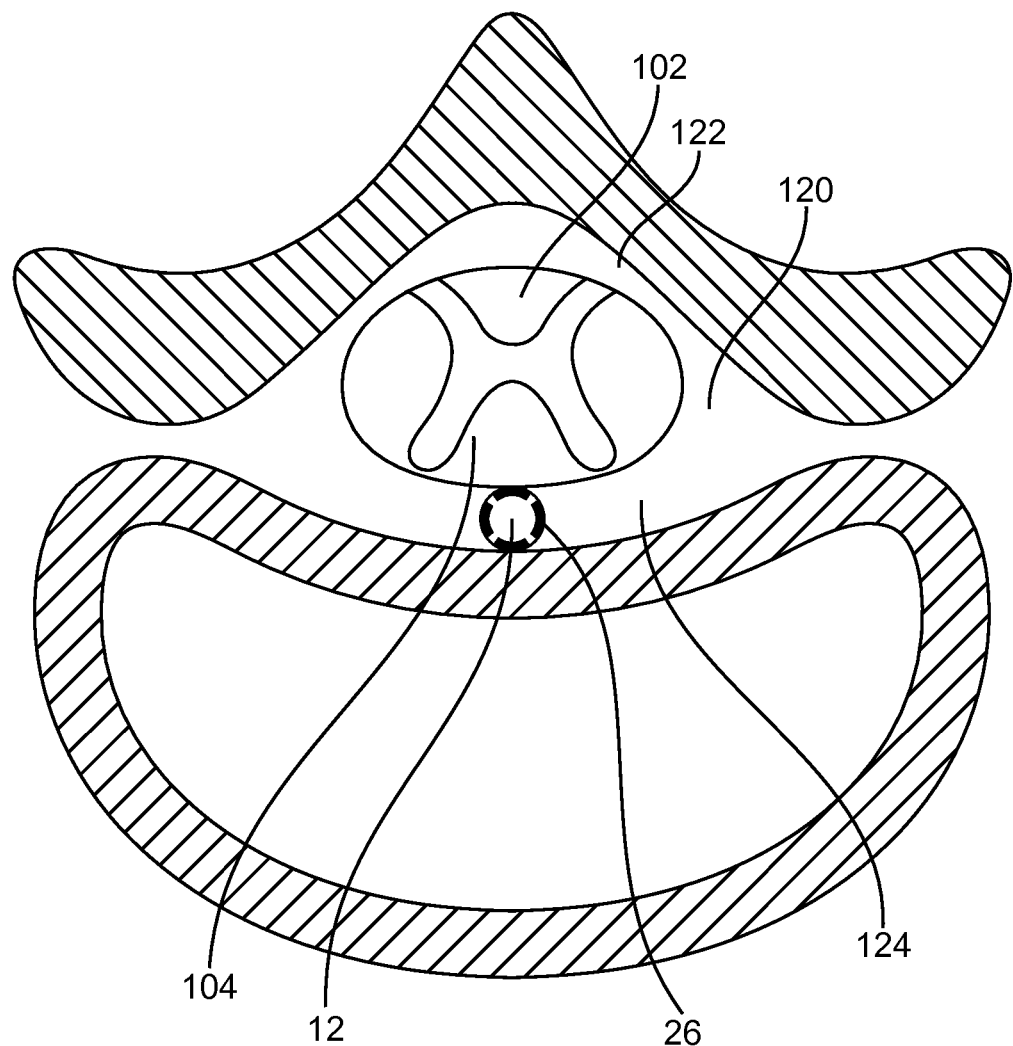
FIG. 6B is a cross-sectional view of the spinal cord showing the placement of a segmented ring electrode on a cylindrical stimulation lead in accordance with the present inventions.
Figure 6C:
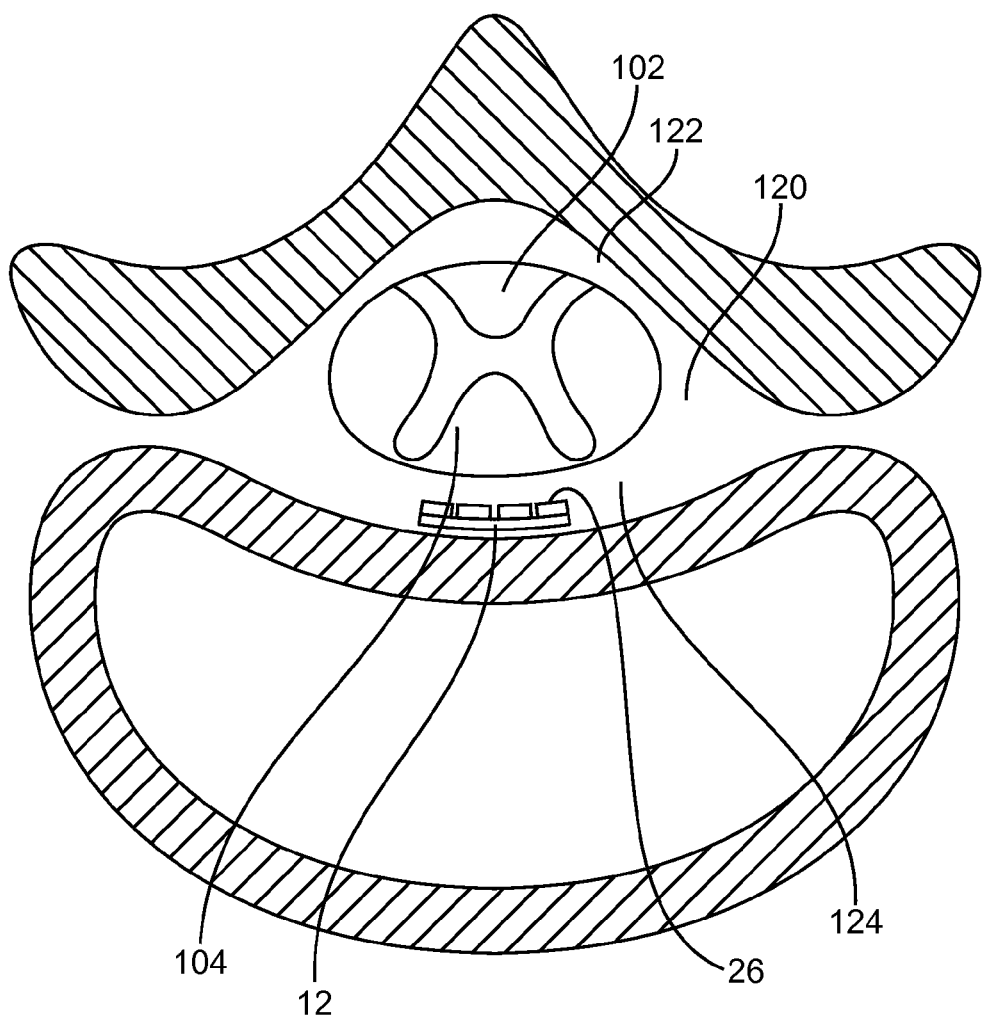
FIG. 6C is a cross-sectional view of the spinal cord showing the placement of electrodes on a paddle lead in accordance with the present inventions.

As discussed above with reference to FIG. 1, in prior art SCS techniques for treating motor disorders, stimulation is applied to the dorsal column 102 and the lead 12 is positioned in the dorsal region 122 of the epidural space 120. In accordance with the present inventions, to more effectively treat symptoms of motor disorders, stimulation is applied to the ventral column 104. In order to apply stimulation to the ventral column 104, the stimulation lead 12 is positioned in the ventral portion 124 of the epidural space 120, as shown in FIGS. 6A-6C. With the lead 12 positioned in the ventral portion 124 of the epidural space 120, stimulation applied through the electrodes 26 on the lead 12 is applied to the ventral column 104. The stimulation is such that at least one affected ventral column nerve fiber innervates the peripheral region of the patient's body that exhibits the symptoms of the motor disorder.

As discussed above with reference to FIGS. 4A-4D, various lead and electrode configurations may be used in the present invention. For example, the cylindrical lead 12 with ring electrodes 26 shown in FIG. 4A is positioned in the ventral portion 124 of the epidural space 120, as depicted in FIG. 6A. In another example, the cylindrical lead 12 having segmented ring electrodes 26 shown in FIGS. 4B-4C is positioned in the ventral portion 124 of the epidural space 120, as depicted in FIG. 6B. In yet another example, the paddle lead 12 having electrodes 26 disposed on the same side of the lead 12 as shown in FIG. 4D is positioned in the ventral portion 124 of the epidural space 120, as depicted in FIG. 6C. Regardless of the electrode and lead configuration, the leads 12 are positioned within the ventral portion 124 of the epidural space 120 with at least a portion of the electrodes 26 facing the spinal cord 100.

A method 200 for performing a medical procedure on a patient having a motor disorder affecting a peripheral region of the patient's body will be described with reference to FIG. 7. First, in step 202, the stimulation lead 12 is introduced within the ventral portion 124 of the epidural space 120 (see, e.g., FIGS. 6A-6C). Next, in step 204, the lead 12 is positioned such that at least a portion of each of the electrodes 26 faces toward the patient's spinal cord 100. For example, if the electrodes 26 are ring electrodes as shown in FIGS. 4A and 6A, the electrode 26 faces the spinal cord 100 regardless of the orientation of the lead 12. If the electrode 26 is a segmented ring electrode (as depicted in FIGS. 4B-4C and 6B), the lead 12 is positioned so that one of the segments of the electrode 26 faces the spinal cord 100. If the lead 12 is a paddle lead (as depicted in FIGS. 4D and 6C), the paddle lead is positioned so that the electrodes 26 on the paddle lead face towards the spinal cord 100. Finally, in step 206, the lead 12 is affixed with the portion of each of the electrodes 26 facing the spinal cord 100, e.g., by suturing the lead to connective tissue. The lead 12 is affixed such that the electrodes 26 are located at an area of the spinal cord 100 having a ventral column nerve fiber that innervates the peripheral region of the patient's body that is affected by the motor disorder.

Figure 7:
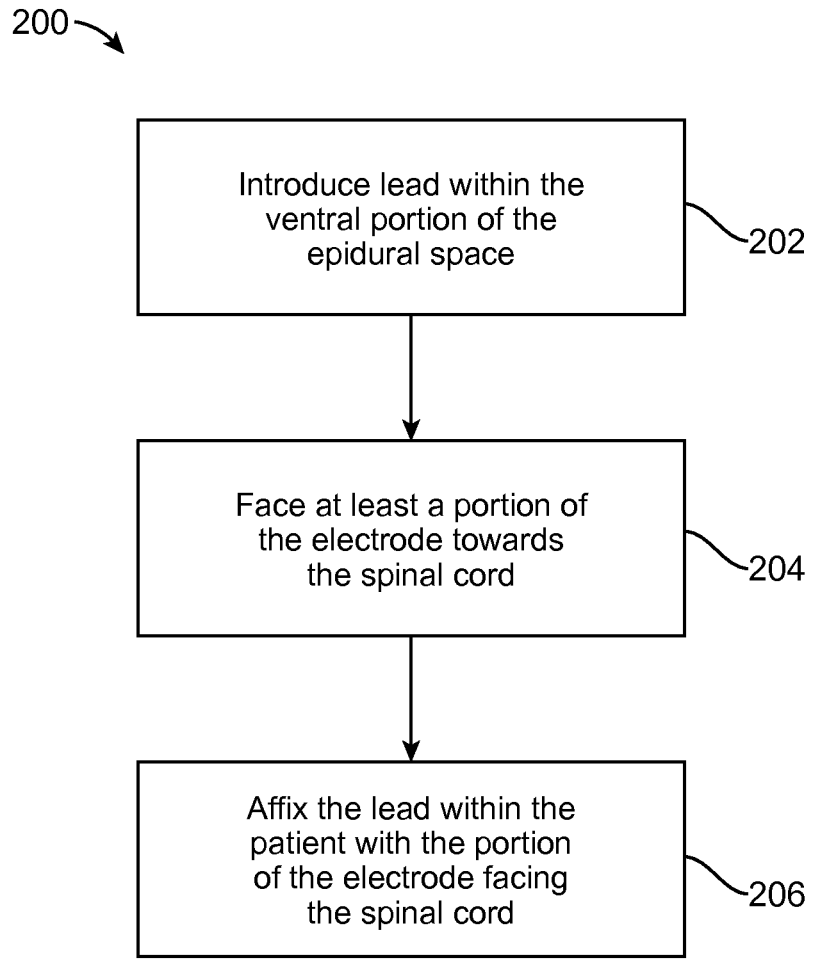
FIG. 7 is a flow chart illustrating a method of performing a medical procedure on a patient suffering from a motor disorder.

After the procedure depicted in FIG. 7 is performed, electrical stimulation energy may be applied to a ventral column nerve fiber of the patient. The ventral column nerve fiber to which the stimulation is applied innervates the peripheral region exhibiting the symptoms of the motor disorder. The applied electrical stimulation energy may inhibit nerve impulses traveling from the patient's brain to the peripheral region, thereby treating the symptoms of the motor disorder.

The electrical stimulation energy may be applied according to one or more stimulation strategies. Exemplary stimulation strategies include high frequency stimulation (e.g., above 100 Hz) having a narrow pulse width (e.g., below 20 μs). The electrode combination is such that the field is highly confined to activate midline or specific target tracks, or nearby structures. For example, the electrode combination may include a narrow guarded cathode or a transverse tripole. The amplitude of the stimulation may be adjusted up to motor threshold and then adjusted to a submotor level. Exemplary mechanisms for stimulating ventral nerves for treating symptoms of motor disorders may include (1) modulating descending information through high frequency stimulation, or (2) antidromic firing of descending axons to create a "reset" effect on brain neurons.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method for of performing a medical procedure on a patient suffering from a motor disorder, the method using a stimulation lead having at least one electrode, the method comprising:
introducing a stimulation lead having at least one electrode within a ventral portion of an epidural space of the patient;
facing at least a portion of the at least one electrode toward a spinal cord of the patient; and
affixing the lead within the patient, such that the portion of the at least one electrode faces the spinal cord.

2. The method of claim 1, wherein the lead is affixed parallel to the spinal cord.

3. The method of claim 1, wherein the lead is a paddle lead and the at least one electrode comprises a plurality of electrodes disposed on the same side of the paddle lead.

4. The method of claim 1, wherein the motor disorder affects a peripheral region of the patient, and wherein the lead is affixed such that the at least one electrode is located at an area of the spinal cord having a ventral column nerve fiber that innervates the peripheral region.

5. The method of claim 1, wherein the lead is a cylindrical lead and the at least one electrode comprises a plurality of radially segmented electrodes.

6. The method of claim 1, wherein the lead is a cylindrical lead and the at least one electrode comprises a plurality of ring electrodes.

7. A method for providing therapy to a patient suffering from a motor disorder using at least one electrode implanted within a ventral portion of an epidural space of the patient, the method comprising:
applying electrical stimulation energy to at least one ventral column nerve fiber of the patient, thereby treating symptoms of the motor disorder.

8. The method of claim 7, wherein the applied electrical stimulation energy inhibits nerve impulses traveling from the patient's brain to a peripheral region exhibiting the symptoms of the motor disorder.

9. The method of claim 7, wherein the motor disorder affects a peripheral region of the patient, and wherein the at least one ventral column nerve fiber innervates the peripheral region.

10. The method of claim 7, wherein the electrical stimulation energy is applied at a frequency above 100 Hz.

11. The method of claim 7, wherein the electrical stimulation energy is applied at a pulse width of less than 20 μs.

* * * * *